United States Patent [19]

Bresson et al.

[11] Patent Number: 4,459,237

[45] Date of Patent: Jul. 10, 1984

[54] TRITHIOCARBONATES

[75] Inventors: Clarence R. Bresson; Robert M. Parlman; James B. Kimble, all of Bartlesville, Okla.

[73] Assignee: Phillips Petroleum Company, Bartlesville, Okla.

[21] Appl. No.: 328,340

[22] Filed: Dec. 7, 1981

[51] Int. Cl.$^3$ .......................................... C07C 154/02
[52] U.S. Cl. .................................... 260/455 B; 75/2; 252/60
[58] Field of Search .................................... 260/455 B

[56] References Cited

U.S. PATENT DOCUMENTS

| | | | |
|---|---|---|---|
| 2,020,021 | 11/1935 | Farrington et al. | 260/455 B |
| 2,203,739 | 6/1940 | Ott | 260/455 B |
| 2,600,737 | 6/1952 | Crouch et al. | 260/455 |
| 3,425,551 | 2/1969 | Baarson et al. | 289/166 |
| 4,316,797 | 2/1982 | Parlman | 252/61 |
| 4,341,715 | 7/1982 | Parlman et al. | 209/166 |

FOREIGN PATENT DOCUMENTS 275915  10/1970  U.S.S.R. .............................. 209/166

OTHER PUBLICATIONS

Ind. and Eng. Chem., vol. 42, No. 5, pp. 918–919, (May 1950).

Primary Examiner—John M. Ford
Assistant Examiner—Robert C. Whittenbaugh

[57] ABSTRACT

The efficiency of metals separation using ore flotation is improved by the use of certain substituted hydrocarbylene trithiocarbonates as suppressants for undesired metals.

11 Claims, No Drawings

TRITHIOCARBONATES

BACKGROUND

This invention relates to novel compounds and their use in flotation processes for recovering minerals from their ores. In another aspect of the invention it relates to the recovery of molybdenum-bearing minerals from their ores. In another aspect of the invention it relates to the use of flotation agents and flotation depressants in the recovery of minerals from their ores.

Froth flotation is a process for concentrating minerals from ores. In a froth flotation process, the ore is crushed and wet ground to obtain a pulp. Additives such as collecting, or mineral flotation agents and frothing agents are added to the pulp to assist in subsequent flotation steps in separating valuable minerals from the undesired portions of the ore. The pulp is then aerated to produce a froth at the surface. The minerals which adhere to the bubbles or froth are skimmed or otherwise removed and the mineral-bearing froth is collected and further processed to obtain the desired minerals. Frequently, other chemicals are added to the separated mineral-bearing froth to assist in subsequent separations particularly when significant proportions of two or more minerals are present in the separated mineral-bearing froth. Such chemicals are known as depressants. These materials are sometimes referred to more appropriately as deactivators and are used selectively to separate one type of mineral from another type of mineral.

THE INVENTION

The invention deals with a group of novel compounds and their use, alone or in combination with other substances, as reagents in ore flotation processes. One embodiment deals with a process in which a metallurgical concentrate containing molybdenum-bearing compounds is admixed in a froth flotation process with an amount of one or more substituted salts of organo-trithiocarbonates sufficient to depress the flotation of the copper- and iron-bearing materials.

OBJECTS OF THE INVENTION

It is one object of the invention to provide a class of compounds which are useful as flotation suppressants in ore flotation processes.

It is another object to provide a process for the recovery of molybdenum-containing substances from ores containing mixtures of molybdenum-bearing minerals and minerals bearing other metals via a froth flotation procedure in which the flotation of copper and iron are suppressed by contacting the ore with the compounds used herein.

It is still another object of this invention to provide ore separation processes employing both flotation agents and flotation depressants.

Other aspects and objects of this invention will become apparent upon reading this specification and the appended claims.

ADVANTAGES OF THE INVENTION

Unlike commercial suppressants, such as NaCN, NaSH, thioglycolic acid and Nokes solution (i.e., $P_3S_5$/NaOH), the suppressant reagents used herein do not release hazardous gases, such as cyanides and hydrogen sulfide, into the atmosphere.

Furthermore, the compounds used in the invention can be used in smaller quantities than the quantities required for the efficient use of conventional suppressants.

In one embodiment of the invention in an ore flotation process employing collector reagents for the separation of molybdenum, an improvement is made by employing carboxyalkyl trithiocarbonates as suppressants of pyrite and copper. Carboxymethyl trithiocarbonate permits an 84% recovery of Mo with a recovery of only 3% Fe and 30% Cu. When a commercial suppressant blend of NaCN and Nokes solution is used instead of the carboxymethyl trithiocarbonate the Mo recovery is 85.5% but the Fe recovery is 5.2% and the Cu recovery is 68.3%.

DESCRIPTION OF THE INVENTION

The novel compounds used as separation reagents herein are ammonium, Group IA, or Group IIA metal salts of substituted hydrocarbyl trithiocarbonates. They conform to the general formula:

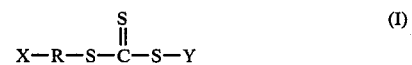

wherein X is selected from —OH, —COOH, and —COOY; R is a $C_{1-20}$ organic moiety; and Y is a Group IA or IIA metal ion or an ammonium ion. Generally, they are salts of carboxy-substituted organo trithiocarbonates.

A preferred group of compounds are the salts of carboxyalkyltrithiocarbonates conforming to the formula:

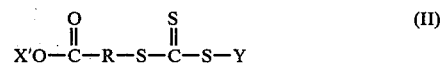

where X' is selected from —H, and —Y and R and Y have the meanings given above. These salts can be prepared by well-known techniques. One technique is represented by the equation

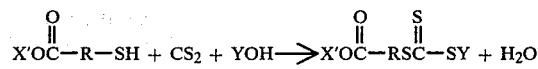

wherein X', R, and Y have the designations recited above.

In Formula (II) above, it is preferred that X' be such that a —COOM substituent in which M is lithium, sodium, postassium, calcium, or magnesium is present on the organic moiety. It is highly preferred that M be sodium.

The organic moiety, R, in the reagents of the invention can be any organic moiety which contains from 1 to about 20 carbon atoms and serves to link X— with the —SCSSY groups. Typically, R is a hydrocarbylene moiety. Useful moieties include alkylene linkages, such as methylene, ethylene, and tertiary butylene groups, and aromatic linkages, such as phenylene, methyl phenylene, methylene phenylene, phenylene methylene, and naphthylene. While it is preferred that R be an unsubstituted hydrocarbylene moiety, R may carry other substituents which do not interfere with the function of the reagents as suppressants in froth flotation processes. Preferably, R is an alkylene group containing from 1 to about 12 carbon atoms.

At least one Y substituent is attached to the terminal sulfur atom of the trithiocarbonate. While Y may be an —$NH_4$ ion or any Group IA or Group IIA metal ion, it is preferred that Y be a Group IA metal ion. Sodium is highly preferred.

One preferred group of separation reagents used herein are compounds in which X' and Y are identical. Exemplary of such compounds are disalts such as:
S-ammonium-O-ammonium-3-carboxypropyl trithiocarbonate,
S-ammonium-O-ammonium-4-carboxyphenyl trithiocarbonate,
S-sodium-O-sodium carboxymethyl trithiocarbonate,
S-sodium-O-sodium-2-carboxyethyl trithiocarbonate,
S-sodium-O-sodium-3-carboxypropyl trithiocarbonate,
S-sodium-O-sodium-6-carboxyhexyl trithiocarbonate,
S-sodium-O-sodium-2-carboxydodecyl trithiocarbonate,
S-sodium-O-sodium-4-carboxyphenyl trithiocarbonate,
S-sodium-O-sodium-2-carboxy-2-methyl-2-butylethyl trithiocarbonate
S-sodium-O-sodium-p-carboxybenzyl trithiocarbonate
S-sodium-O-sodium-m-carboxymethylphenyl trithiocarbonate
and the like, and mixtures thereof.

Mixtures of any of the reagents described by formula I as well as mixtures of these with other conventional separation reagents are useful in this invention. Flotation or collecting agents useful in this invention can be chosen from any of the known operable compounds among which are xanthates, dithiophosphates, dithiocarbamates, thiols (mercaptans), thiocarbanilide, fatty acid soaps, arenesulfonates or alkylarenesulfonates, alkyl sulfates, primary amines, quaternary ammonium salts, and alkylpyridinium salts. The preferred flotation agents are the alkali metal alkyl xanthates. Among the suitable alkali metal alkyl xanthates which may be used are the potassium or sodium salts of ethyl xanthate, isopropyl xanthate, butyl xanthate, amyl xanthate, hexyl xanthate, cetyl xanthate and the like.

The amount of flotation agent employed varies considerably depending on the type of flotation agent employed, the pH, and the type of mineral being floated (etc. sulfide, oxide, etc). For sulfide mineral flotation, generally only about 0.01 to about 0.1 lbs. of xanthate is required per ton of ore.

The amount of carboxyorganotrithiocarbonate salt employed as a suppressant for one or more minerals can vary widely. Generally, the quantity used depends on the amount of flotation or collecting agent employed, the flotation technique used, and on the amount and kinds of minerals present in the ore. When molybdenum is in high concentration (i.e., the primary ore body), the range of trithiocarbonate used can be from about 0.01 to 0.1 lbs. per ton of ore used. When the molybdenum is in low concentration, (i.e., a primary Cu ore body), the range of trithiocarbonate used can be from about 0.1 to 5 lbs. per ton of concentrate. In one preferred embodiment of the instant invention carboxyalkyl trithiocarbonates are used to suppress the flotation of Cu, Fe and "insols" (Ca and Mg silicates) in the presence of molybdenum.

The molybdenum-bearing minerals found in these ores include such substances as molybdenite, $MoS_2$, and wulfenite $PbMoO_4$. These and other molybdenum-containing materials can be isolated from the minerals-containing froth while the flotation of the less desirable minerals is suppressed by the reagents of the invention.

Any froth flotation apparatus can be used in this invention. The most commonly used commericial flotation machines are the Agitair (Galigher Co.), Denver D-2 (Denver Equipment Co.), and the Fagergren (Western Machinery Co.). Smaller, laboratory scale apparatus such as the Hallimond cell can also be used.

The instant invention was demonstrated in tests conducted at ambient room temperature and atmospheric pressure. However, any temperature or pressure generally employed by those skilled in the art is within the scope of this invention.

EXAMPLES

The following examples serve to illustrate the operability of this invention.

EXAMPLE I

This example describes the preparation of the hydroxy- and carboxyalkyl trithiocarbonates described herein. This procedure is typical for all compounds prepared. To a 3-neck glass flask fitted with a condenser, stirrer, thermometer and dropping funnel was added 180 milliliters of water and 42 grams (1.05 moles) of sodium hydroxide. After cooling to below 50 C., 53 grams (0.5 mole) of 3-mercaptopropionic acid was slowly added with stirring over a 20 minute period. The mixture was cooled to below 45 C. whereupon 38 grams (0.5 mole) of carbon disulfide was slowly added over a 30 minute period. The cloudy mixture was maintained with stirring at 45 C. for 1.5 hours at which time the solution became clear. The bright orange clear solution was cooled to room temperature and bottled. The solution was calculated to be 40 wt. percent of the disodium salt of 2-carboxyethyl trithiocarbonic acid referred herein also as S-sodium-O-sodium-2-carboxyethyl trithiocarbonate.

There was similarly prepared a 40 wt. percent aqueous solution of the disodium salt of carboxymethyl trithiocarbonic acid from 42 grams (1.05 moles) of sodium hydroxide, 144 milliliters of water, 46 grams (0.5 moles) thioglycolic acid and 38 grams (0.5 grams) of carbon disulfide. Likewise there was prepared a 40 wt. percent aqueous solution of the monosodium salt of 2-hydroxyethyl trithiocarbonic acid from 22 grams (0.55 mole) sodium hydroxide, about 140 milliliters water, 39 grams (0.5 mole) 2-hydroxyethyl mercaptan and 38 grams (0.5 mole) carbon disulfide.

EXAMPLE II

This example describes an alternate method of preparing the S-sodium-O-sodium of carboxymethyl trithiocarbonate which may offer economical advantages over the method of Example I. To a 300 milliliter capacity stainless steel stirred reactor was added 30 grams of water and 20 grams (0.5 mole) sodium hydroxide. The reactor was closed and hydrogen sulfide (16 grams, 0.47 moles) was slowly pressured into the reactor over about a 20 minute period. Cooling was applied through cooling coils to maintain the temperature below 38 C. The pressure on the reactor was 70 psig. Carbon disulfide (19 grams, 0.25 mole) was slowly added with cooling and stirring over a 50 minute period, the temperature being about 28 C. and the pressure 60 to 75 psig. A solution comprised of 58 milliliters water, 10 grams (0.25 mole) sodium hydroxide and 23.5 grams (0.25 mole) of chloroacetic acid was pumped into the reactor over a 30 minute period while maintaining the temperature below 35 C. The pressure on the reactor slowly rose to 145 psig by the end of the addition. After the addition was complete, the mixture was heated to 50 C. for 1 hour with stirring, cooled to about 25 C. and discharged to give 146 grams of effluent product calculated to be about 40 wt. percent aqueous solution of disodiocarboxymethyl trithiocarbonate (includes the trithiocarbonate, water, and sodium chloride).

EXAMPLE III

This example is a control describing a standard ore flotation process with and without a copper and iron suppressant (e.g. Nokes Reagent). The example describes the procedure used herein to evaluate the mining chemicals. To a ball mill was charged 1005 grams of primary molybdenum-containing ore from Amax Mines, Climax, Colo. along with 0.3 grams lime, 500 milliliters water, pine oil (0.027 lbs/ton ore), Syntex (0.05 lbs/ton ore) a sulfonated coconut oil from Colgate-Palmolive, vapor oil (0.38 lbs/ton ore), sodium silicate (0.66 lbs/ton ore), and Nokes reagent (0.03 lbs/ton ore) aqueous $P_2S_5$/NaOH to suppress copper and iron flotation. The mixture was ground for 4 minutes 8 seconds to give a particle size distribution of 35%+100 Tyler mesh screen size. The mixture was transferred to a Denver D-2 flotation along with enough water to make a 20 wt. percent aqueous solids mixture. An additional 0.03 lbs/ton ore of Nokes solution was added and the mixture was conditioned for 2 minutes while being stirred at 1000 RPM. Air was introduced into the pulp through the agitator at 42.5 cubic feet per minute. The concentrate was scraped off with a paddle at about 25 strokes per minute for a float of 5 minutes. After flotation, the concentrate was dried and analyzed. The procedure was repeated several times. In the first repeat Nokes solution was omitted. In the second repeat, thiodiglycol was substituted for the Nokes solution and in the third repeat, disodium carboxymethyl trithiocarbonate (supplied as a 40 wt. percent aqueous solution) was substituted for the Nokes solution. These results which are listed in Table I show the disodium carboxymethyl trithiocarbonate greatly reduces the amount of iron and copper floated as compared to the other systems employed while maintaining a higher but at least comparable amount of molybdenum recovery.

TABLE I

Suppression of Fe and Cu in a Mo-Bearing Ore Flotation Process

| Suppressant (.03 lbs/ ton in Grind and Cell) | Rougher Concentrate | | | | | |
|---|---|---|---|---|---|---|
| | Grams | | | % in Concentrate | | |
| | Fe | Cu | Mo | Fe | Cu | Mo |
| Control-No suppressor | 0.926 | .083 | 1.57 | 4.03 | .36 | 6.81 |
| Nokes-$P_2S_5$/NaOH | 1.530 | .038 | 1.63 | 5.23 | .13 | 5.59 |
| Thiodiglycol | 1.490 | .087 | 1.68 | 5.13 | .30 | 5.74 |
| S—Sodium-O—Sodium Carboxymethyl Trithiocarbonate | 0.490 | .012 | 1.45 | 2.75 | .07 | 8.16 |

EXAMPLE IV

This example contains inventive runs illustrating the effect of carboxyalkyl trithiocarbonate salts as suppressants (or collectors) on the separation of iron, copper and molybdenum by flotation. The general procedure described in Example III was followed but with a few minor changes. For example, to the grind was added 1005 grams of ore, 497 milliliters of water, lime (0.2 lbs/ton ore), pine oil (0.037–0.052 lbs/ton ore), Syntex (0.05 lbs/ton ore, sodium silicate (0.66 lbs/ton ore), and vapor oil (0.38 lbs/ton ore. There were 3 floats made for each run. The suppressant (or collector) at 0.04 lbs/ton ore was added before the first float. Before each of the second and third floats was added additional Syntex (0.02 lbs/ton ore) and 0.16 lbs/ton ore of vapor oil. Each float was 2 minutes. When Nokes reagent (0.03 lbs/ton ore) was used, it was added at the grind stage. The results of these runs are listed in Table II wherein it can be seen that the carboxyalkyl trithiocarbonate salts suppress the flotation of iron and especially copper significantly better than does a commericailly available copper and iron suppressant, Nokes reagent. The data also shows that 2-hydroxyethyl trithiocarbonate salt, an analog to the inventive carboxyalkyl trithiocarbonates, does not suppress copper or iron. In fact the data seems to indicate the hydroxyalkyl trithiocarbonate actually enhances the flotation of iron. In addition, the data indicates the carboxyalkyl trithiocarbonates perform better as iron suppressants in the absence of Nokes reagent. Also, the data indicates the carboxyethyl trithiocarbonate is a better Cu suppressant than the carboxymethyl trithiocarbonate, whereas the carboxymethyl trithiocarbonate is a better Fe suppressant than the carboxyethyltrithiocarbonate.

TABLE II

Suppression of Fe and Cu in a Mo-Bearing Ore Flotation Process

| No. | Nokes[a] #/Ton | Suppressant, 0.04 lbs/Ton Ore | % Recovery | | |
|---|---|---|---|---|---|
| | | | Fe | Cu | Mo |
| 1. | .03 | None-Control | 5.15 | 68.30 | 85.50 |
| 2. | — | None-Control | 7.70 | 65.10 | 79.00 |
| 3. | .03 | S—Sodium-2-Hydroxyethyl trithiocarbonate | 22.20 | 63.90 | 84.60 |
| 4. | .03 | S—Sodium—O—Sodium-2-Carboxyethyl trithiocarbonate | 4.24 | 24.49 | 80.49 |
| 5. | — | S—Sodium—O—Sodium-2-Carboxyethyl trithiocarbonate | 3.44 | 21.91 | 75.48 |
| 6. | .03 | S—Sodium—O—Sodium-Carboxymethyl trithiocarbonate | 3.16 | 28.03 | 83.19 |
| 7. | — | S—Sodium—O—Sodium-Carboxymethyl trithiocarbonate | 2.76 | 30.08 | 84.19 |

[a]Nokes reagent is aqueous $P_2S_5$ and NaOH.

Reasonable variations, such as would occur to one of the ordinary skill in the art, may be made herein without departing from the scope of the invention.

We claim:

1. As new compounds, substituted hydrocarbyl trithiocarbonates of the general formula

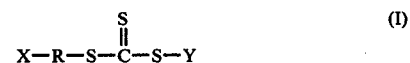

wherein X is selected from a —OH, —COOH, and —COOY; R is a $C_{1-20}$ hydrocarbylene moiety selected from the group consisting of alkylene and hydrocarbyl arylene; and Y is a Group IA metal ion, a Group IIA metal ion, or an ammonium ion.

2. The compounds of claim 1 wherein Y is a Group IA metal ion.

3. The compounds of claim 2 wherein Y is sodium.

4. The compounds of claim 1 wherein R is an alkylene moiety and X is —COOY where Y is alkali or alkaline earth metal.

5. The compounds of claim 4 wherein Y is a Group IA metal ion.

6. The compounds of claim 5 wherein X is —COOY.

7. S-sodium-O-sodium-2-carboxyethyl trithiocarbonate.

8. S-sodium-O-sodium-carboxymethyl trithiocarbonate.

9. The compounds of claim 1 wherein R is an alkylene moiety and X is a hydroxyl group.

10. The compounds of claim 2 wherein R is an alkylene moiety and X is a hydroxyl group.

11. S-sodium-2-hydroxyethyl trithiocarbonate.

* * * * *